(12) United States Patent
Takada

(10) Patent No.: US 6,224,544 B1
(45) Date of Patent: May 1, 2001

(54) SELF-PROPELLED COLONOSCOPE AND CLEANING PROCESS THEREOF

(76) Inventor: Masazumi Takada, 622-26 Takatsukashinden, Matsudo-city, Chiba 270-2222 (JP)

( * ) Notice: Subject to any disclaimer, the term of this patent is extended or adjusted under 35 U.S.C. 154(b) by 0 days.

(21) Appl. No.: 09/303,878

(22) Filed: May 3, 1999

(30) Foreign Application Priority Data

Aug. 26, 1998 (JP) .................................................. 10-254695
Apr. 7, 1999 (JP) .................................................. 11-099600

(51) Int. Cl.[7] ...................................................... A61B 1/12
(52) U.S. Cl. ......................... 600/155; 600/114; 600/101; 600/139; 600/156
(58) Field of Search ..................................... 600/153, 155, 600/156, 133, 101, 104, 114, 115, 116

(56) References Cited

U.S. PATENT DOCUMENTS 4,561,427 * 12/1985 Takada ...................................... 128/4
5,562,601 * 10/1996 Takada .................................. 600/114
6,071,234 * 6/2000 Takada .................................. 600/114

FOREIGN PATENT DOCUMENTS 8-38416    2/1996 (JP) .

* cited by examiner

Primary Examiner—Michael Peffley
Assistant Examiner—Jocelyn Debra Ram
(74) Attorney, Agent, or Firm—Young & Thompson

(57) ABSTRACT

An endoscope is provided, being insertable in the colon of a patient, in a self-propelled manner, by driving a plurality of endless belts mounted along the outside surface of a flexible section of an insertion tube thereof, and having a cleaning mechanism therein to be easily cleaned after use. A self-propelled colonoscope (1) is an endoscope insertable in the colon by driving endless belts (10) mounted along the almost entire length of a flexible section (4) of an insertion tube (5), and having guide pipes, which guide returning endless belts, being mounted in the insertion tube thereof, each of said guide pipes being provided with an opening for a cleaning brush (35) and a casing (31), which surrounds the endless belt driving unit, being formed with a cleaning window (33), said window being provided with a lid (37).

2 Claims, 8 Drawing Sheets

SELF-PROPELLED COLONOSCOPE AND CLEANING PROCESS THEREOF

BACKGROUND OF THE INVENTION

The present invention relates to a self-propelled colonoscope, which does not cause pain to a patient during colono-endoscopic examination for the colon, and a cleaning process for the colonoscope. More particularly, it relates to an improved endoscope, which is insertable into the colon, in a self-propelling manner, by driving a plurality of endless belts mounted along the outside of a flexible section of an insertion tube thereof, and wherein a mechanism for easy cleaning after use is provided, and it also relates to a cleaning process thereof.

Colonoscopes which can self-propel along with the shape of the colon of a patient, without causing pain to the patient, have been proposed. The inventor of the present invention disclosed in Japanese Patent Laid-open No.8-38416 an endoscope capable of self-propelling in the colon of a patient by driving a plurality of endless belts mounted along the outside of a flexible section of an insertion tube thereof.

The disclosed colonoscope is provided with a plurality of endless belts along the substantially entire length of the outside surface of the flexible section of the insertion tube. The endless belts are to be driven by a driving mechanism mounted at the driving unit of the colonoscope, and the outer circles of the endless belts touch the wall of the colon, so that friction between the colon wall and said endless belts will allow the distal end of the colonoscope to move spontaneously forward in the inside of the colon. The inner circle of each of the endless belts passes through one of the guide pipes, provided in the flexible section of the insertion tube, and is led to the distal end of the flexible section of the insertion tube, and comes out to the outside surface of the insertion tube again, and the endless belts therefore rotate endlessly. With the endless belts contacting the colon wall, the colonoscope can move spontaneously forward in the colon without excessive extending or bending of the colon. The disclosed colonoscope is smoothly insertable into the colon, keeping the position and shape of the colon relatively in the intact condition, so that little pain may be caused to the patient.

The disclosed colonoscope, however, has a lot of parts necessary to be cleaned after use, such as endless belts, guide pipes, and drive rollers, because these parts are exposed to patient's body fluid. The endless belts, especially, will be adhered to by body fluid or excretion because of their direct contact with the colon wall. Further, the guide pipes, in which the endless belts pass, tend to be contaminated by the belts. Still further, the drive rollers are in contact with the endless belts and may be consequently contaminated.

SUMMARY OF THE INVENTION

In view of above problems, it is an object of the present invention to provide a colonoscope which is insertable in the colon, in a self-propelling manner, by driving a plurality of endless belts mounted at the outside surface of a flexible section of an insertion tube and has a mechanism therein to be easily washable after use, and also to provide a cleaning process for the colonoscope.

According to a first aspect of the present invention, a colonoscope is insertable in the colon, in a self-propelling manner, by driving an endless belt mounted at the outside surface of a flexible section of an insertion tube thereof. The colonoscope comprises a guide pipe, which forms a guide way for a returning endless belt in the flexible section of the insertion tube, said guide pipe having an opening, provided at least one end thereof, for insertion of a cleaning brush.

While being washed, the guide pipe may be cleaned inside by taking a cleaning brush in and out of the opening, after the endless belt is removed.

According to a second aspect of the present invention, a colonoscope is insertable in the colon, in a self-propelling manner, by driving an endless belt mounted at the outside surface of a flexible section of an insertion tube thereof. The colonoscope comprises a cleaning window at a casing surrounding a driving unit of the self-propelled colonoscope, said window having a lid for opening and closing the casing.

The inside of the casing containing drive rollers therein can be washed by immersing the colonoscope in a cleaning solution in a washing vessel, with keeping the lid open. During cleaning, an electric apparatus, such as a motor, may be placed above the surface of the cleaning solution.

In a cleaning process of the self-propelling colonoscope according to the first aspect of the present invention, a colonoscope is insertable in the colon, in a self-propelling manner, by driving an endless belt mounted at the outside surface of a flexible section of an insertion tube thereof. The colonoscope comprises a guide pipe, which forms a guide way for a returning endless belt in the flexible section of the insertion tube, said guide pipe having an opening, provided at least one end thereof, for insertion of a cleaning brush. A cleaning brush is inserted in said opening as to wash the inside of the guide pipe after the endless belt is removed.

Said guide pipe contaminated by the endless belt will be washed by taking a cleaning brash in and out of the guide pipe.

In a cleaning process for the self-propelling colonoscope according to the second aspect of the present invention, a colonoscope is insertable in the colon, in a self-propelling manner, by driving an endless belt mounted at the outside surface of a flexible section of an insertion tube thereof. The colonoscope comprises a cleaning window provided at the casing surrounding the endless belt driving unit, said window having a lid for opening and closing the casing. With said cover kept open, the colonoscope is to be immersed in the cleaning solution in the washing vessel.

The cleaning solution is fed into the casing through the cleaning window. The drive roller or the inside of the guide pipe will be immersed in the solution and washed. The cleaning window is usually closed by the lid.

DETAILED EMBODIMENTS OF THE INVENTION

Referring to the attached drawings, the detailed embodiments of the present invention will be set forth.

Figure 1:
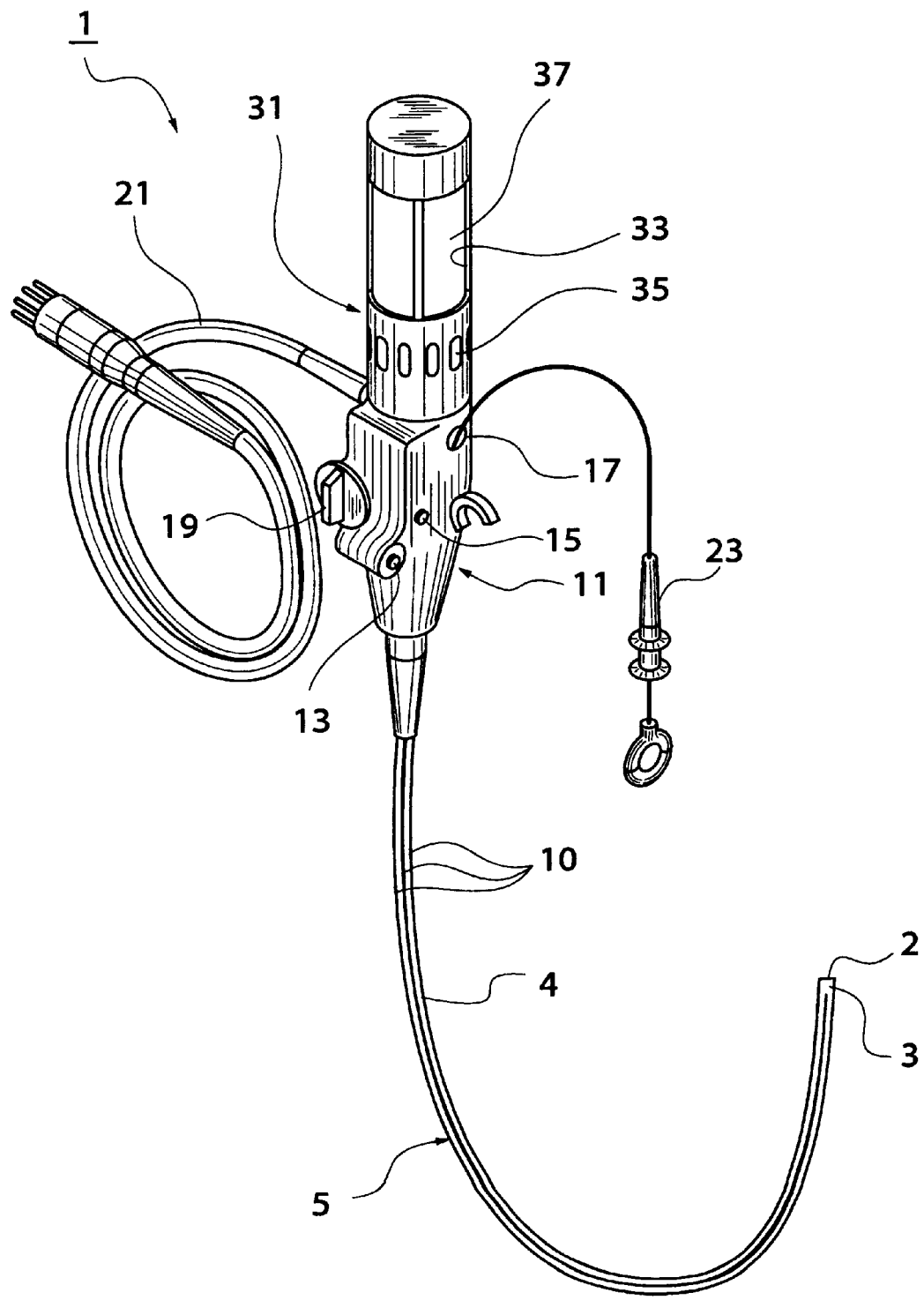
FIG. 1 shows a perspective view of the outer appearance of a self-propelled colonoscope according to one embodiment of the present invention.

FIG. 1 shows a perspective view of the outer appearance of the self-propelled colonoscope according to one embodiment of the present invention.

A self-propelled colonoscope 1 is provided with an insertion tube 5 comprising a distal section 2, a bending section 3, and a flexible section 4, a plurality of endless belts 10, an operation unit 11, and a casing 31 containing belt drive rollers therein.

The basic construction of the self-propelled colonoscope 1 is now set forth as below.

The self-propelled colonoscope 1 comprises a belt driving section 50 at its upper portion protected by the casing 31, and the operation unit 11 connected to the bottom of the casing 31, and further comprises the insertion tube 5, extending form the operation unit 11. The insertion tube 5 comprises the distal section 2, the bending section 3, and the flexible section 4. The bending section 3 can be flexed in all directions by adjusting a control knob 19, mounted at the operation unit 11.

Figure 4:
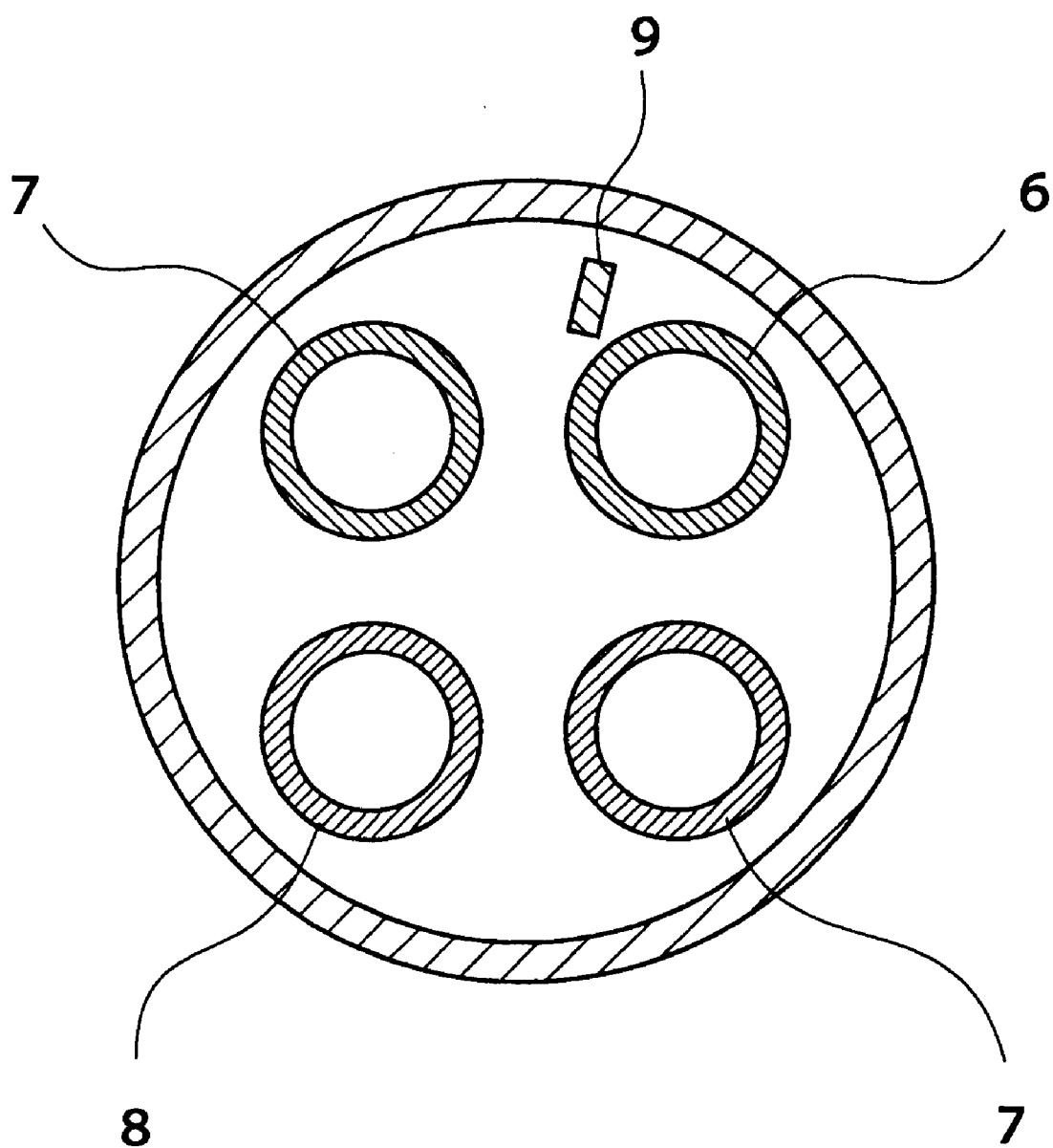
FIG. 4 shows a front view of the distal end of the insertion tube of the endoscope according to the embodiment.

The distal section 2 of the insertion tube 5 is provided, as shown in FIG. 4, with an image receiving window 6, two light projecting windows 7, a suction and forceps opening 8, and an air-water nozzle 9.

The image-receiving window 6, equipped with an objective lens for a fiberscope, or an image pick-up device for an electronic scope, such as a CCD, receives an image from the distal end of the tube. The received image is transmitted to the operation unit 11 by an image guide of a fiberscope or lead wire of an electronic scope, which is inserted in the insertion tube 5, and then transferred to a display through an universal cord 21. A light guide such as an optical fiber, inserted in the bore of each of the light projecting windows 7, runs through the operation unit 11, via the universal cord 21, and is connected to a light source outside. The light source projects light from the distal end surface of the light guide.

The suction and forceps opening 8 is connected to a forceps insertion opening 17 at the operation unit so that a forceps 23 can be inserted in. The tip ends of the forceps 23, protruding from the distal end of the insertion tube 5, are manipulated by the proximal end of the forceps 23 as to treat a patient or collect a part of tissue of the patient. The bore of the air-water nozzle 9 is a water-air supply channel, and air or a cleaning solution is injected through the air-water nozzle 9 by manipulating the air-water supply button 13 of the operation unit 11. Through the suction and forceps opening 8, body fluid or cleaning solution remaining in the colon is sucked out and excreted to the outside of patient's body. This operation is carried out by the suction control valve 15 at the operation unit 11.

Figure 3:
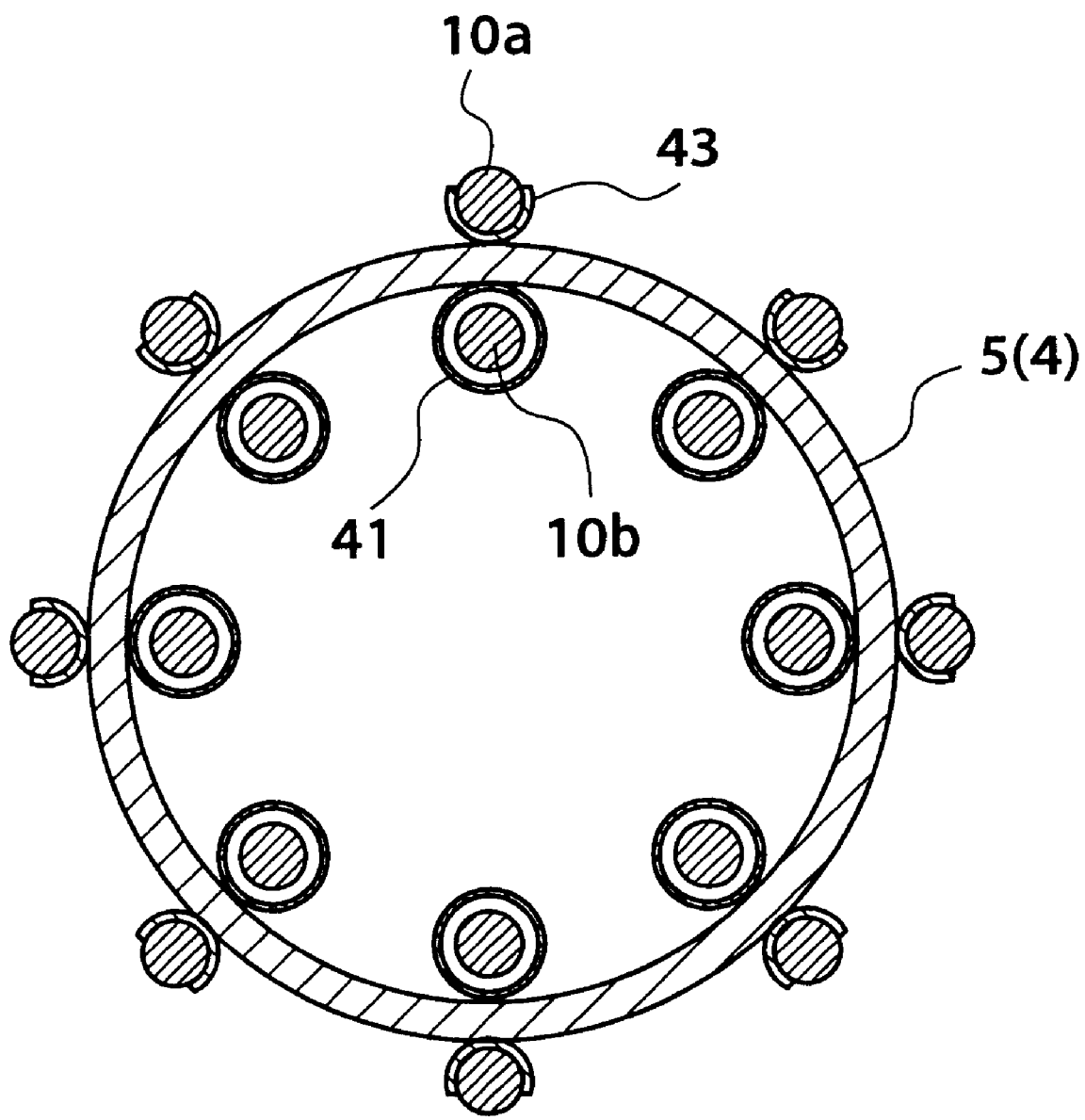
FIG. 3 shows a sectional view of the flexible section of the insertion tube of the endoscope according to the embodiment.

A plurality of endless belts 10 is mounted longitudinally on the outside surface of the flexible section 4 of the insertion tube 5. The diameter of the flexible section 4 is preferably 5 to 30 mm, and it is also preferable that the number of the endless belt 10 is larger, because the larger the number of the endless belts is, the higher the self-propelling performance of the colonoscope becomes. As shown in FIG. 3, the outside portion 10a of the endless belt 10 is supported by a guide hook 43, formed on the outside surface of the tube 5. The inside portion 10b of the endless belt passes through a guide pipe 41 in the insertion tube 5. Each of the guide hooks 43, having a section whose shape is an arc of larger than 180°, is longitudinally mounted at the flexible section 4 so that a portion of each of the endless belts exposed from each of the guide hooks will be positioned radially and outwardly; the outer circle of the endless belt 10 supported by the guide hook 43 is shown at the outside of the guide hook 43. When being inserted into the colon, the endless belts can keep a sufficient contacting area with the colon wall. Even when the flexible section 4 is severely looped, the endless belts will not be off the guide hooks 43.

Each of the endless belts 10, the diameter of whose section is a circle of 1 to 3 mm or the width of whose section is a belt-like shape of 1 to 3 mm, is made of a flexible and strong material such as, for instance, carbon fiber or resin. It is preferable for the back side of each of the endless belts to be coated with a material having high friction resistance as to rotate synchronously with the drive roller 51, shown in FIG. 2, or to have a rack formed.

During cleaning a colonoscope, each of the endless belts thereof needs to be removed from the insertion tube, and it thus has a mechanism to be removed and reattached. The detail of the mechanism will be described later.

Figure 2:
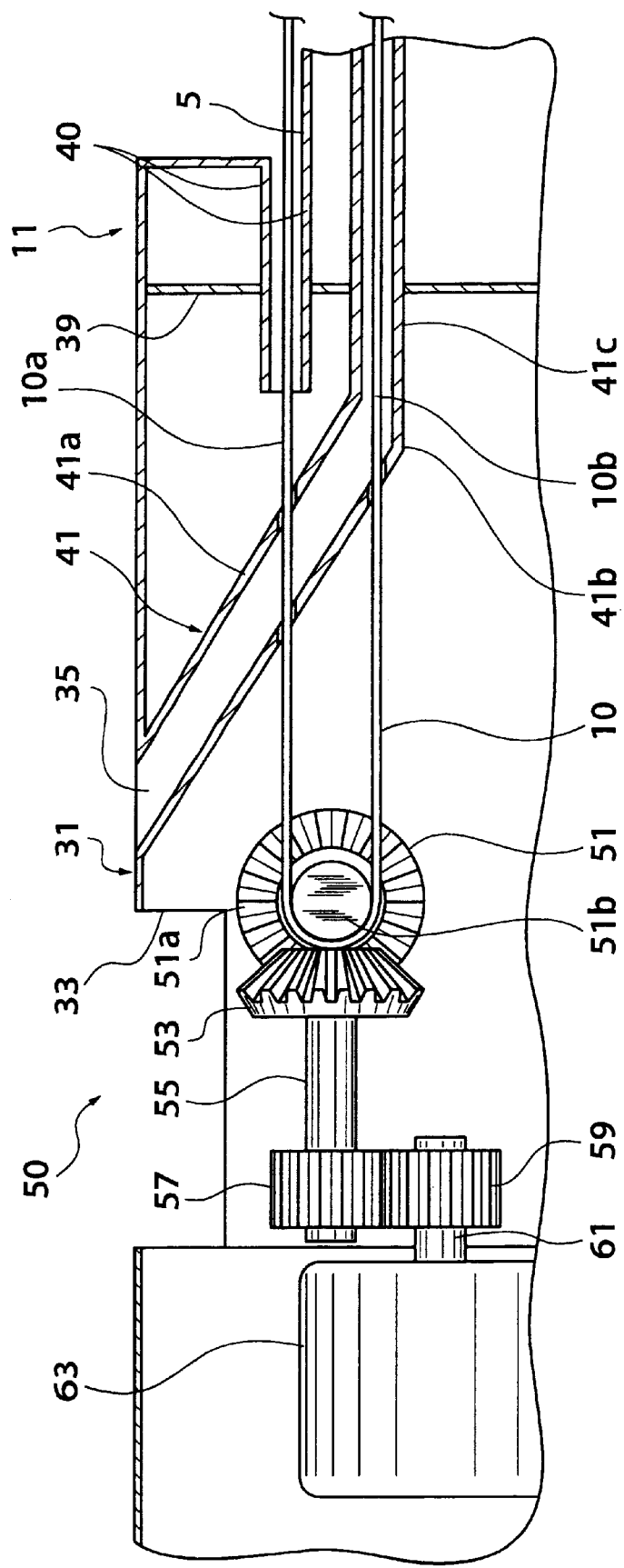
FIG. 2 shows a side sectional view around the driving unit of the endoscope according to the embodiment.

Referring now to FIG. 2, the construction of the proximal part of the guide pipe 41 and the driving unit of the endless belt will be set forth.

The proximal section of the guide pipe 41 is connected to the guide pipe opening 35 formed in the side of the casing 31. The casing is bigger than the insertion tube 5 in diameter. The guide pipe 41 comprise a ramp (inclined section) 41a, extending diagonally from the guide pipe opening 35 formed in the side of the casing 31 to the insertion tube 5. The guide pipe 41 also comprises a guide section 41c, running through from the ramp 41a to the bending section 41b and extending straight in the insertion tube 5.

Figure 5:
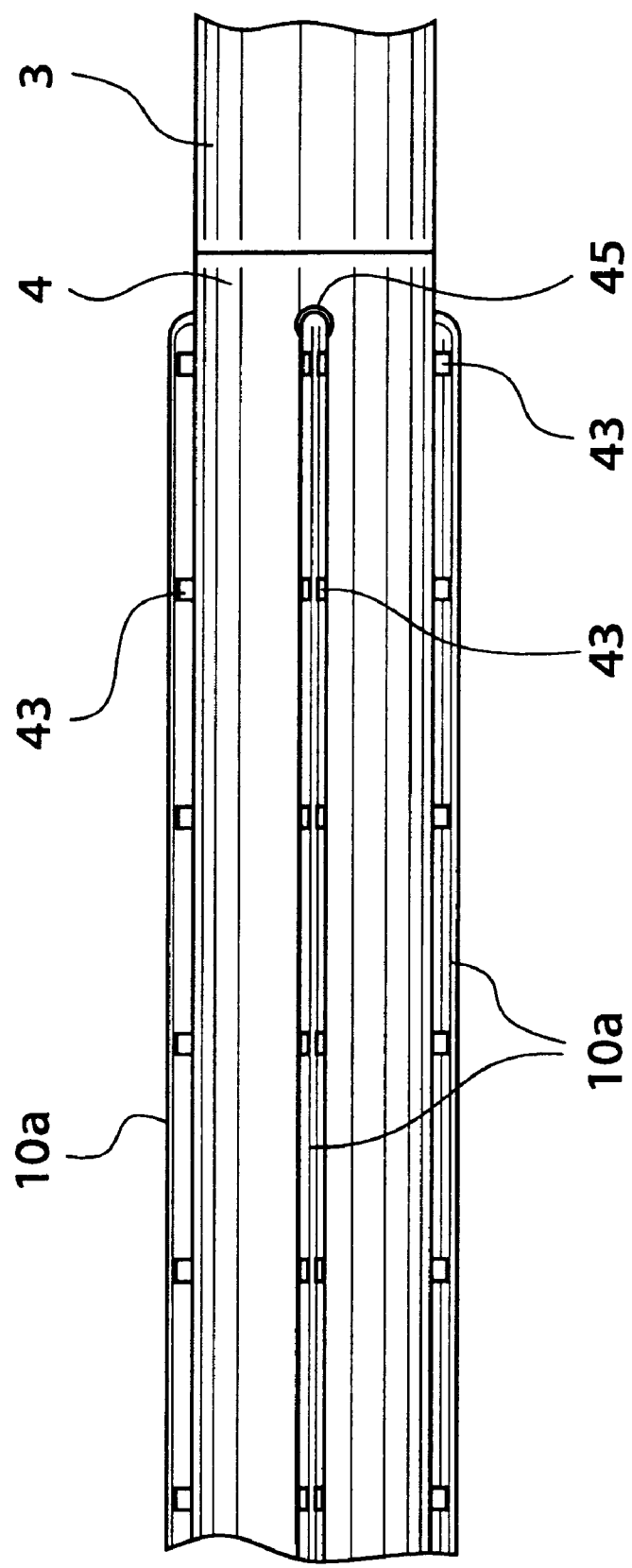
FIG. 5 shows a side view of a portion around the distal end of the flexible section of the insertion tube of the endoscope according to the embodiment.

The drive roller 51, pinching the endless belt 10, is mounted on the outside of the proximal end of the guide pipe 41 in the casing 31 of the driving unit. The endless belt 10 is penetrating the side wall of the guide pipe 41 at the ramp 41a of the guide pipe 41. That is, the exterior portion 10a of the endless belt 10, running into the guide section 40 from the outside surface of the insertion tube 5 and then crossing two holes formed at the side wall of the ramp 41a of the guide pipe, extends toward the proximal end. The proximal portion of the endless belt 10 is wound and held by the drive roller 51. On the other hand, the interior portion 10b of the endless belt 10 runs at the inside of the guide pipe 41, penetrating the side wall of the guide pipe 41 at the inside of the ramp 41a of the guide pipe 41. The interior portion 10b of the endless belt 10 is led, via the pipe 41, to the guide hole 45, formed around the distal end of the flexible section 4 of the insertion tube 5. The guide hole 45, as shown in FIG. 5, is positioned at 0 to 10 cm from the distal end of the flexible section 4. This is because the bigger the part where the inside wall of the colon is in contact with the outside portion 10a of the endless belt 10 is, the higher the performance of self-propelling of the self-propelled colonoscope becomes.

The drive roller 51 comprises a pulley 51b, wound by the endless belt 10, and a bevel gear 51a, connected to the same axis as is the pulley 51b. The endless belt 10 and the pulley 51b are engaged together by friction or a rack function. A bevel gear 53 being engaged with the bevel gear 51a is orthogonally arranged. A spur gear 57, which is fixed to the proximal section of the gear axis 55 of the bevel gear, will be engaged with a large spur gear 59 fixed to the motor axis 61 of a motor 63. Consequently, when the motor shaft 61 revolves by driving the motor 63, the bevel gear 51*a* will revolve, via the large spur gear 59, the spur gear 57, and the bevel 53, and accordingly the pulley 51*b* will revolve.

On the circumference of the large spur gear 59, the same number of the drive rollers 51, the bevel gears 53, the gear shafts 55, and the spur gears 57 as the endless belts 10 are mounted in the same configuration.

The motor 63, the large spur gear 59, the spur gear 57, the gear shaft 55, the bevel gear 53, and the drive roller 51 are mounted in the casing 31 of the driving unit at the proximal end beyond the guide pipe opening 35. On the side of the casing 31 of the driving unit is formed with a cleaning opening 33. Said opening 33 is provided with a lid 37, shown in FIG. 1, and can be open or closed.

The pulley 51*b* is so rotated counterclockwise by driving the motor 63 that the endless belt 10 being engaged with the pulley 51*b* will rotate counterclockwise as well. At this time, if the outer circle of the endless belt 10 is in contact with the inside wall of the colon, the insertion tube will be fed forward the right direction of FIG. 2 by friction between the endless belt 10 and the inside wall of the colon. The insertion tube 5 moves backward by rotating the motor 63 clockwise.

The guide section 40 is also provided at the outside 10*a* of the endless belt, which is shown at the outside surface of the insertion tube 5, up to the flexible section 4 as to prevent the cleaning solution from going in to the operation unit 11 during cleaning. In addition, the driving unit 50 and the operation unit 11 are isolated from each other by the wall 39 surrounding the guide pipe 41 and guide section 40, so that the cleaning solution will not get in the operation unit 11.

A cleaning process for the self-propelled colonoscope 1 according to the embodiment of the present invention will be described.

Figure 6:
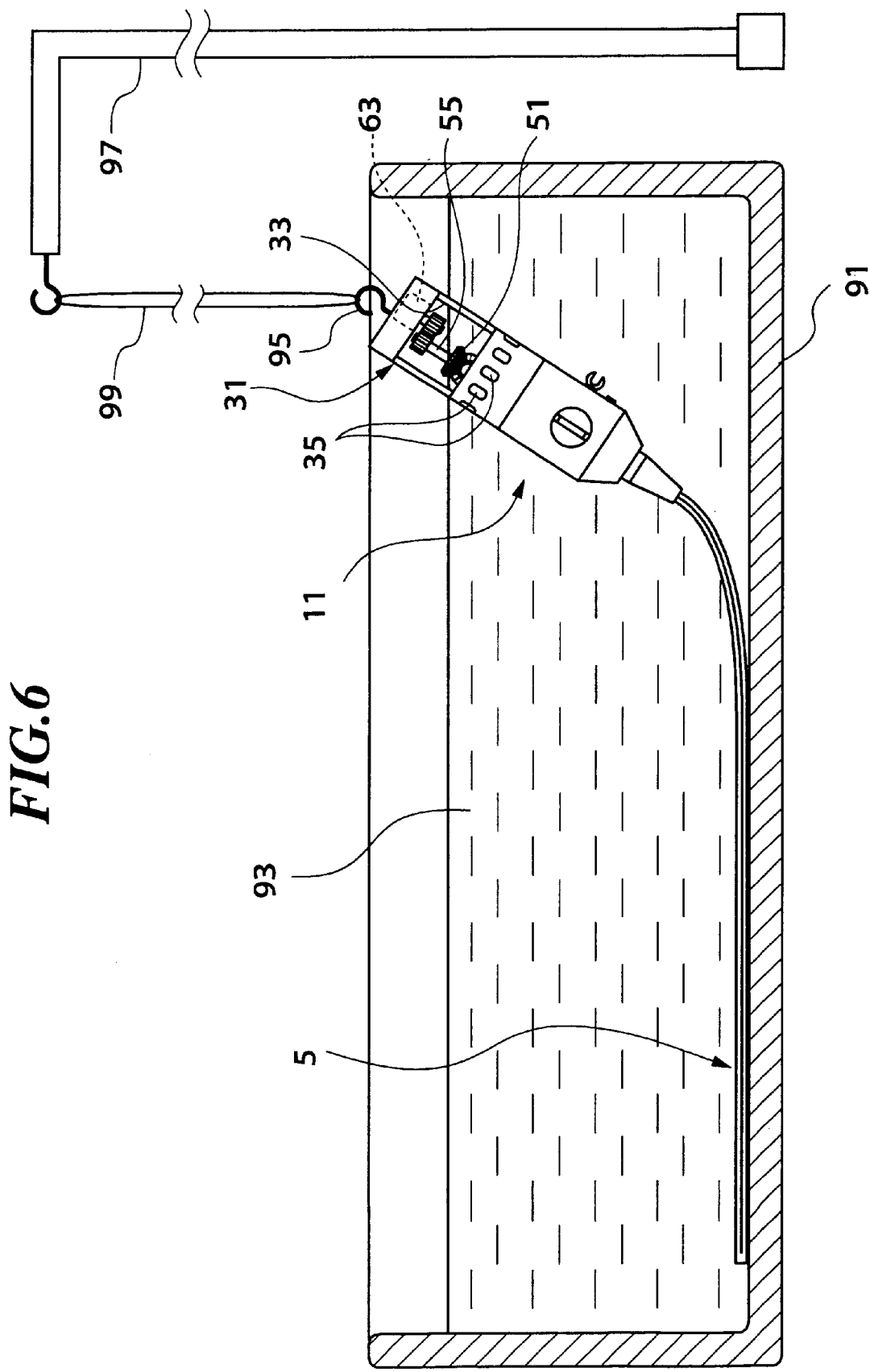
FIG. 6 shows a view wherein the endoscope of the embodiment is being cleaned.

FIG. 6 is a drawing showing a condition such that the colonoscope according to the present invention is being cleaned.

First, all the endless belts are cut and removed from the insertion tube 5. Then, a cleaning brush is inserted in from the guide pipe opening 35, formed at the casing 31 of the driving unit, and taken in and out the inside of the guide pipe 41. Thus, body fluid or excreta adhered to the inside of the guide pipe 41 will be removed. By providing a detachable and attachable part on a certain portion of the endless belt, with using a magnet or a melting material at low temperatures, the endless belt may be reusable.

The insertion tube 5, the operation unit 11, and a lower portion of the driving unit casing 31 will be immersed in a washing vessel 91 filled with a cleaning solution 93, with the lid 37 of the casing 31 of the driving unit kept open. At this time, by being observed from the cleaning opening 33, the colonoscope should be held in a manner such that the drive roller 51 in the casing of the driving unit, which directly pinches the endless belt, is surely immersed in the cleaning solution, and the motor 63 is placed above the solution surface. As shown in FIG. 6, when the gear shaft 55 is immersed in the cleaning solution 93, the solution will get in the driving unit 50 from the cleaning opening 33, then to the inside of the guide pipe 41 and guide section 40 (referring to FIG. 2). The drive roller 51 is also immersed in the cleaning solution. That is, the surface area of the insertion tube 5, the inside and outside of the guide pipe 41, a portion from the guide pipe opening 35 to the distal end of the flexible section of the insertion tube 5, the guide section 40, and the drive roller 51 are all together to be immersed in the cleaning solution 93. All the mentioned-above portions are soaked 5 minutes in the cleaning solution 93, which a proteolytic enzyme generally is used for, and then soaked 10 minutes in a sterilizing solution for endoscopes, such as a Glutaral agent. The removed endless belts are also cleaned by soaking in the cleaning solution. A string 99 is hooked on a hook 95 formed at the casing 31 of the driving unit, and using another stand 97 to hang the string may reduce labor.

Figure 7:
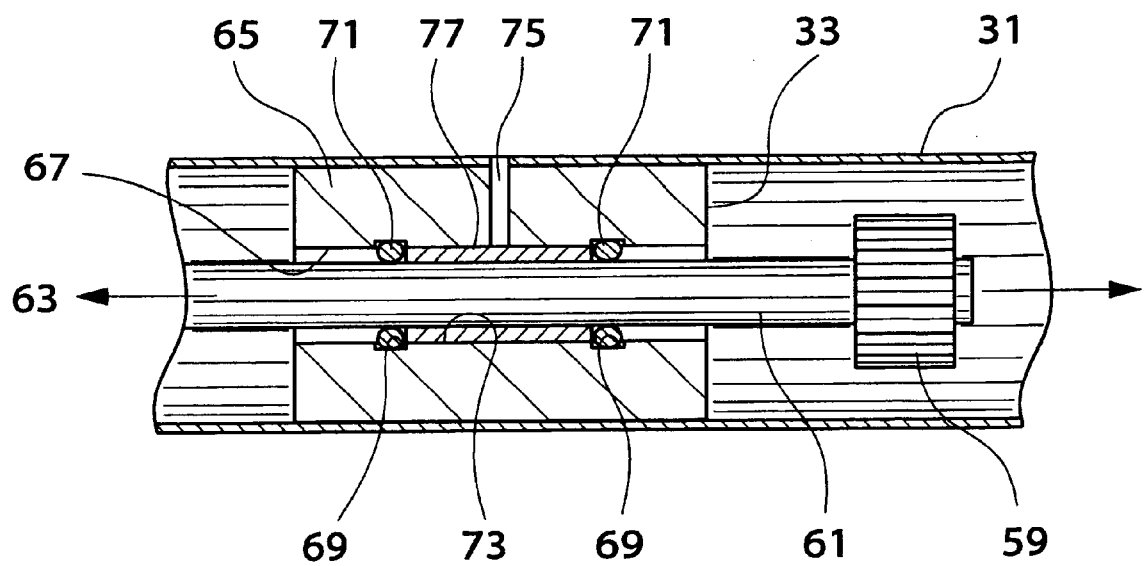
FIG. 7 shows a side sectional view of the driving unit of the endoscope according to another embodiment of the present invention.

FIG. 7 shows a side sectional view of the driving unit of the self-propelled colonoscope according to another embodiment of the present invention.

In the driving unit of this embodiment, electric apparatuses such as a motor and a group of gears necessary to be cleaned are sealed in fluid-tight condition.

A housing 65, having a bore 67 where a motor shaft 61 penetrates, is mounted in a portion between the motor 63 and a reduction gear 59 in the casing 31 of the driving unit. The housing 65, made of plastics and the like, whose outer circumference is fixed to the casing 31 of the driving unit in a fluid-tight manner. The bore 67 of the housing 65 is so made a little bigger than the motor shaft in diameter that the motor shaft is freely rotatable. Two o-ring grooves are axially formed along the inner circumference at the center of the bore 67. Each of o-ring grooves 69 is mounted with a rubber-made o-ring 71 surrounding the motor shaft 61. A portion between the two o-ring grooves is a little bigger diametered hollow section 73. The hollow section 73, through the hydraulic port 75 charged with rubber, is connected to the outer surface of the casing of the driving unit toward the motor.

The hollow section 73 of the housing 65 is charged with hydraulic oil 77 by pressure of around one barometric pressure with a needle through the hydraulic port 75. The charged hydraulic oil 77 is surrounded by the two o-rings 71 and therefore sealed in the hollow section 73. The passage in the hydraulic port of the needle will be closed due to elasticity of the rubber after drawing the needle off. Since the oil has relatively high viscosity, a film is formed between the o-rings 71 and motor 61, so that a seal against a cleaning solution will be provided. Consequently, when the colonoscope of the present invention, including the motor 63, is immersed in a cleaning solution, the solution will not get in the inside of the motor 63 because of the oil 77 around the motor shaft 61 having the pressure equivalent to the pressure of the cleaning solution.

Figure 8:
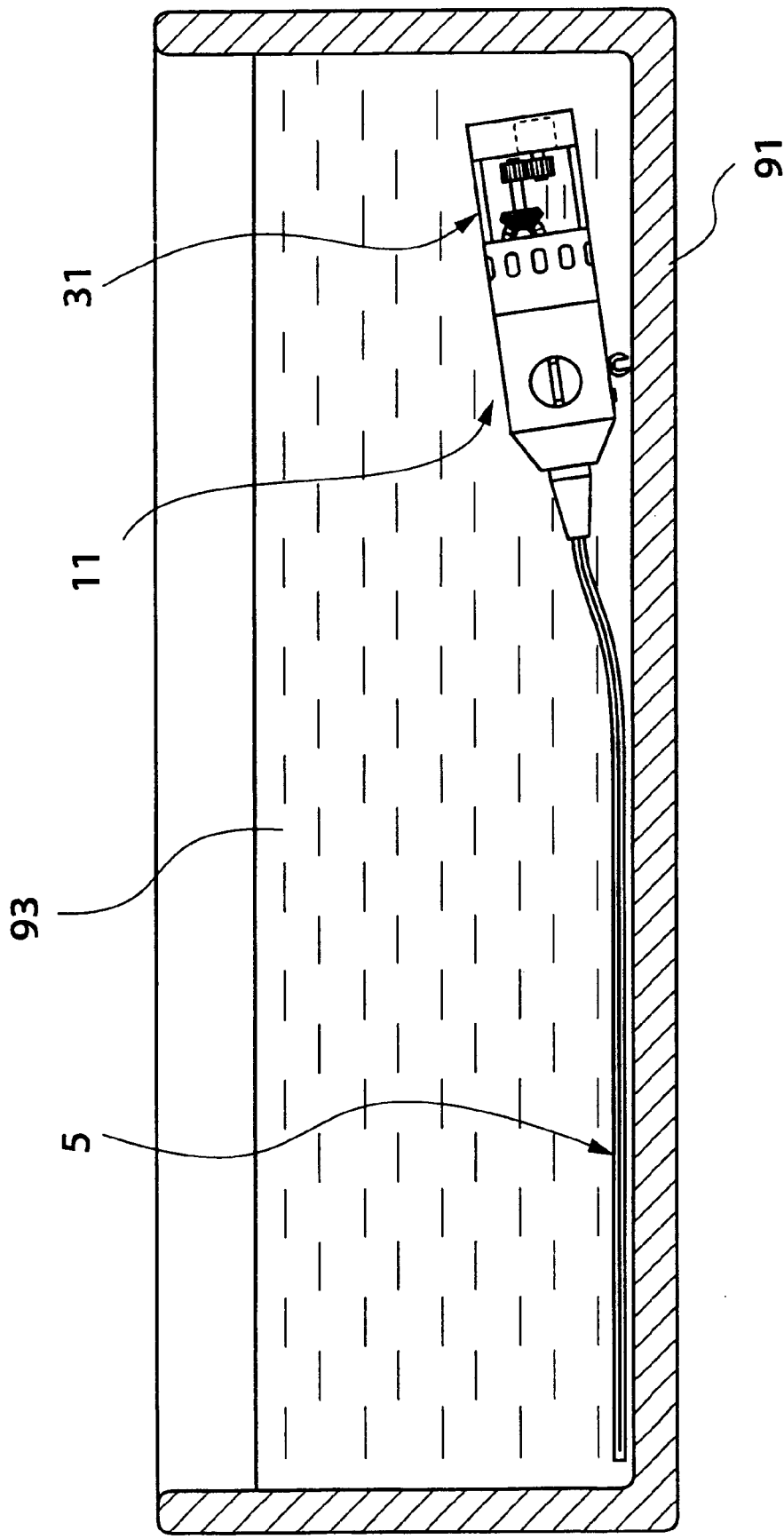
FIG. 8 shows a view wherein the endoscope shown in FIG. 7 is being cleaned.

FIG. 8 shows a condition such that the colonoscope is being cleaned according to the embodiment of FIG. 7.

All the portions of the self-propelled colonoscope are immersed in the cleaning solution 93, placed lying down at the bottom of the washing vessel, and the portion including the motor 63, as mentioned above, is also immersed in the solution. Under this condition, the motor 63 is isolated from the cleaning opening 33 by the hydraulic oil 77 in the casing 65 surrounding the motor shaft 61, as shown in FIG. 7. The pressure of the hydraulic oil 77 is the same as that of the cleaning solution 93 so that the cleaning solution within the casing 31 of the driving unit will not go into the casing of the motor containing electric apparatuses.

Thus, cleaning of the self-propelled colonoscope can be easily carried out by soaking the colonoscope in the washing vessel 91, without care to oversee electric apparatuses, such as a motor, not to be immersed in the solution.

In light of the above description, the present invention can provide an endoscope which is insertable, in a self-propelled manner, in the colon by driving endless belts mounted along the outside surface of a flexible section of an insertion tube and which has a mechanism, in which the colonoscope can be easily cleaned after use, and a cleaning process thereof.

While the invention has been particularly shown and described with reference to preferred embodiment thereof, it will be understood by those skilled in the art that various changes can be made therein without departing from the spirit and scope of the invention.

I claim:

1. In a self-propelled colonoscope, insertable in the colon of a patient, in a self-propelled manner, by driving an endless belt mounted along the outside surface of a flexible section of an insertion tube thereof, the improvement comprising:

a cleaning window, being formed in a casing surrounding an endless belt driving unit, said cleaning window being provided with a lid.

2. In a cleaning process for a self-propelled colonoscope, wherein the colonoscope is insertable in the colon of a patient, in a self-propelled manner, by driving an endless belt mounted along the outside surface of a flexible section of an insertion tube thereof, the colonoscope comprising a cleaning window, being formed in a casing surrounding the driving unit of the self-propelled colonoscope, said cleaning window being provided with a lid; and said process comprising the steps of:

opening the lid; and immersing the colonoscope in a washing vessel filled with a cleaning solution.

* * * * *